(12) United States Patent
Liu et al.

(10) Patent No.: US 11,779,294 B2
(45) Date of Patent: Oct. 10, 2023

(54) METHOD, DEVICE AND SYSTEM FOR CALCULATING MICROCIRCULATION INDICATOR BASED ON IMAGE AND PRESSURE SENSOR

(71) Applicant: SUZHOU RAINMED MEDICAL TECHNOLOGY CO., LTD., Jiangsu (CN)

(72) Inventors: Guangzhi Liu, Jiangsu (CN); Zhiyuan Wang, Jiangsu (CN); Wei Dai, Jiangsu (CN); Lin Chen, Jiangsu (CN); Yong Huo, Jiangsu (CN); Yanjun Gong, Jiangsu (CN); Jianping Li, Jiangsu (CN); Tieci Yi, Jiangsu (CN); Bo Zheng, Jiangsu (CN)

(73) Assignee: SUZHOU RAINMED MEDICAL TECHNOLOGY CO., LTD., Suzhou (CN)

( * ) Notice: Subject to any disclaimer, the term of this patent is extended or adjusted under 35 U.S.C. 154(b) by 333 days.

(21) Appl. No.: 17/158,355

(22) Filed: Jan. 26, 2021

(65) Prior Publication Data

US 2021/0145390 A1 May 20, 2021

Related U.S. Application Data

(63) Continuation of application No. PCT/CN2019/115072, filed on Nov. 1, 2019.

(30) Foreign Application Priority Data

Sep. 9, 2019 (CN) .......................... 201910846497.1

(51) Int. Cl.
*A61B 6/00* (2006.01)
*A61B 5/0215* (2006.01)
(Continued)

(52) U.S. Cl.
CPC .............. *A61B 6/504* (2013.01); *A61B 5/026* (2013.01); *A61B 5/0215* (2013.01); *A61B 6/481* (2013.01);
(Continued)

(58) Field of Classification Search
CPC ....... A61B 6/504; A61B 5/0215; A61B 5/026; A61B 6/481; A61B 6/507; A61B 5/02007;
(Continued)

(56) References Cited

U.S. PATENT DOCUMENTS 9,087,147 B1 7/2015 Fonte
2012/0072190 A1* 3/2012 Sharma .................. A61B 5/026
703/2

(Continued)

FOREIGN PATENT DOCUMENTS

CN 102525443 A 7/2012
CN 107730540 A 2/2018
(Continued)

OTHER PUBLICATIONS

International Search Report for parent PCT/CN2019/115072 dated May 27, 2020.
(Continued)

*Primary Examiner* — Siamak Harandi
(74) *Attorney, Agent, or Firm* — Ladas & Parry LLP (57) ABSTRACT

A method, device and system for calculating a microcirculation indicator are provided. A method includes: injecting a vasodilator and subjecting a blood vessel to be measured to coronary angiography; selecting at least one angiographic image of a first body position when the blood vessel to be measured is in a resting state and an angiographic image of a second body position when the blood vessel to be measured is in a dilated state; obtaining a three-dimensional
(Continued)

coronary artery vascular model by three-dimensional modeling; injecting a contrast agent, and obtaining time $T_1$ taken for the contrast agent flowing from an inlet to an outlet of the segment of blood vessel and time $T_2$ taken for the contrast agent flowing from an inlet to an outlet of the segment of blood vessel; obtaining the microcirculation indicator.

9 Claims, 9 Drawing Sheets

(51) Int. Cl.
    *G06T 7/215* (2017.01)
    *A61M 5/00* (2006.01)
    *G06T 7/00* (2017.01)
    *G06T 17/00* (2006.01)
    *G06T 7/62* (2017.01)
    *A61B 5/026* (2006.01)

(52) U.S. Cl.
    CPC ............ *A61B 6/507* (2013.01); *A61M 5/007* (2013.01); *G06T 7/0012* (2013.01); *G06T 7/0016* (2013.01); *G06T 7/215* (2017.01); *G06T 7/62* (2017.01); *G06T 17/00* (2013.01); *G06T 2207/30048* (2013.01); *G06T 2207/30104* (2013.01); *G06T 2207/30172* (2013.01); *G06T 2210/41* (2013.01)

(58) Field of Classification Search
    CPC ...... A61B 6/466; A61M 5/007; G06T 7/0012; G06T 7/0016; G06T 7/215; G06T 7/62; G06T 17/00; G06T 2207/30048; G06T 2207/30104; G06T 2207/30172; G06T 2210/41; G06T 2207/10016; G06T 2207/20036; G06T 2207/20224; G06T 2207/30021; G06T 2207/30101; G16H 30/20

See application file for complete search history.

(56) References Cited

U.S. PATENT DOCUMENTS

| | | | |
|---|---|---|---|
| 2012/0093388 A1* | 4/2012 | Masumoto | ............ G06T 7/0012 382/134 |
| 2014/0024932 A1 | 1/2014 | Sharma et al. | |
| 2017/0068797 A1* | 3/2017 | Sharma | ................ A61B 5/0263 |
| 2019/0110776 A1 | 4/2019 | Yu et al. | |
| 2021/0361176 A1 | 11/2021 | Huo et al. | |

FOREIGN PATENT DOCUMENTS

| | | | |
|---|---|---|---|
| CN | 108550189 | * | 9/2018 |
| CN | 108550189 A | | 9/2018 |
| CN | 108550388 A | | 9/2018 |
| CN | 109770888 A | | 5/2019 |
| CN | 109805949 A | | 5/2019 |
| JP | 2017512577 A | | 5/2017 |

OTHER PUBLICATIONS

Japan Office Action for Application No. 2020-573149, dated Jan. 25, 2022.
China Office Action for Application No. 201910846497.1, dated Jul. 30, 2021.

* cited by examiner

METHOD, DEVICE AND SYSTEM FOR CALCULATING MICROCIRCULATION INDICATOR BASED ON IMAGE AND PRESSURE SENSOR

TECHNICAL FIELD

The present disclosure relates to the field of coronary artery medical technology, and in particular to, a method, a device, a coronary artery analysis system and a storage medium for calculating a microcirculation indicator based on an image and a pressure sensor.

BACKGROUND

The heart is a high energy consumption organ. In a resting state, the oxygen uptake of myocardial metabolism can reach 60% to 80% of the blood oxygen content. Therefore, under stress conditions such as exercise, it is difficult for the heart to meet the increased demand for myocardial hypoxia by increasing the oxygen uptake capacity of the tissue, and in most circumstances, the demand is met by increasing the myocardial blood flow to ensure the oxygen demand for myocardial metabolism. Myocardial microcirculation occupies 95% of the coronary artery circulation. It plays a role in regulating myocardial blood flow through various factors such as local metabolites, endothelium, neuroendocrine, and myogenicity. Studies have shown that abnormal coronary artery microcirculation is an important predictor of poor long-term prognosis in patients suffering from coronary heart disease.

In 2013, the guidelines were changed, and state that for patients with suspected microvascular angina, if there is no obvious abnormality in coronary angiography, they can consider intracavitary injection of acetylcholine or adenosine during the angiography for Doppler measurement to calculate endothelial dependence or non-endothelial dependence CFR, and determine whether there is microcirculation/epicardial vascular spasm", which is provided as a category IIB recommendation.

In 2019, the guidelines have added 1 category IIA recommendation and 2 category IIB recommendations. It is proposed that "for patients with persistent symptoms but normal coronary angiography or moderately narrowed patients with retained iwfr/FFR values, they can consider using microcirculation resistance measurement and/or CFR based on guide wire measurement, which is provided as a category IIA recommendation.

Coronary artery microvascular function is accomplished by detecting the response of capillaries to a vasodilator. The changes in these two aspects of the guidelines also indicate the importance of coronary artery microvascular function tests. The measurement indicator used for coronary artery microvascular function refers to the maximum dilated degree of coronary capillaries, that is, coronary flow reserve (CFR). The vasodilators used mainly comprise non-endothelium independence vasodilators acting on vascular smooth muscle and endothelium dependence vasodilators acting on vascular endothelial cells, including adenosine and acetylcholine.

For patients with no obvious stenosis on coronary angiography but suspected of coronary heart disease (CAD), our previous examination means was injection of adenosine and acetylcholine to detect the response of capillaries to vasodilators. The current examination means mainly comprise coronary fractional flow reserve (FFR) and microcirculation resistance index (IMR).

The measurements of IMR and CFR are made through the pressure guide wire sensor, which incurs the following problems that the distance of the pressure guide wire sensor, the injection speed of saline, the injection volume, and the temperature of the saline will directly affect the measurement results, resulting in inaccurate results and cumbersome measurement process; and a greater impact on patients and severe discomfort due to a long-term continuous injection of vasodilators.

SUMMARY

The present disclosure provides a method, a device, a coronary artery analysis system and a storage medium for calculating a microcirculation indicator based on an image and a pressure sensor, in order to solve the problem of a greater impact on patients and serious discomfort due to a long-term continuous injection of vasodilator during measuring CFR via a pressure wire, a cumbersome process for pressure guide wire measurement, and inaccurate measurement results in the prior art.

In order to achieve the above purpose, in a first aspect, the disclosure provides a method for calculating a microcirculation indicator based on an image and a pressure sensor, comprising:

conventional angiography;

injecting a vasodilator and subjecting a blood vessel to be measured to coronary angiography;

selecting at least one angiographic image of a first body position when the blood vessel to be measured is in a resting state and an angiographic image of a second body position when the blood vessel to be measured is in a dilated state;

selecting a segment of blood vessel from a proximal end to a distal end of the coronary artery for segmentation, and obtaining a three-dimensional coronary artery vascular model by three-dimensional modeling based on the angiographic image of the first body position and the angiographic image of the second body position;

injecting a contrast agent, and obtaining time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position, respectively, according to the three-dimensional coronary artery vascular model and a fluid mechanics formula and the flowing of the contrast agent in the three-dimensional coronary artery vascular model;

obtaining the microcirculation indicator according to $T_1$ and $T_2$.

Optionally, in the above method for calculating a microcirculation indicator based on an image and a pressure sensor, the microcirculation indicator comprises coronary flow reserve CFR, and the $CFR=T_1/T_2$.

Optionally, in the above method for calculating a microcirculation indicator based on an image and a pressure sensor, the times $T_1$ and $T_2$ are calculated according to a ratio of the number of frames of the partial area image into which the heartbeat cycle area is divided to the number of frames transmitted per second.

Optionally, in the above method for calculating a microcirculation indicator based on an image and a pressure sensor, an angle between the first body position and the second body position is greater than 30°.

Optionally, in the above method for calculating a microcirculation indicator based on an image and a pressure sensor, obtaining the three-dimensional coronary artery vascular model by three-dimensional modeling based on the angiographic image of the first body position and the angiographic image of the second body position comprises:

removing an interfering blood vessel in the angiographic images of the first body position and the second body position to obtain a result image;

extracting the coronary artery centerline and diameter of each result image along the extension direction of the coronary artery;

projecting each coronary artery centerline and diameter on a three-dimensional space for three-dimensional modeling to obtain the three-dimensional coronary artery vascular model.

Optionally, in the above method for calculating a microcirculation indicator based on an image and a pressure sensor, the microcirculation indicator comprises: coronary artery microcirculation resistance index IMR;

measuring a coronary artery inlet pressure $P_a$ by a pressure sensor to obtain a pressure drop $\Delta P_i$ from a coronary artery inlet to a stenosed distal end of the coronary artery in the dilated state;

obtaining the coronary artery microcirculation resistance index IMR according to the coronary artery inlet pressure $P_a$, pressure drop $\Delta P_i$, and $T_2$.

Optionally, in the above method for calculating a microcirculation indicator based on an image and a pressure sensor, the IMR=$(P_a-\Delta P_i)\times T_2$.

Optionally, in the method for calculating a microcirculation indicator based on an image and a pressure sensor, measuring the pressure drop $\Delta P_i$ from the coronary artery inlet to the stenosed distal end of the coronary artery comprises:

Subjecting the three-dimensional coronary artery vascular model to a grid division, with the coronary artery centerline as the longitudinal axis, dividing the grid into m points along the coronary artery centerline, and dividing the cross section corresponding to each point of the coronary artery centerline into n nodes, $\Delta P_i$ representing the average value of the pressures of all nodes on the cross section of the i-th point on the coronary center line;

wherein the pressure drop $\Delta P_i$ is calculated using the following formula:

$$\Delta P_i = \frac{\sum_{1}^{n}(P_1 + P_2 + \ldots + P_n)}{n};$$

$P_1$ represents the pressure value of the first node on the cross section of the i-th point in the grids of the three-dimensional vascular model, $P_2$ represents the pressure value of the second node on the cross section of the i-th point in the grids of the three-dimensional vascular model, $P_n$ represents the pressure value of the n-th node on the cross section of the i-th point, and both m and n are positive integers;

the pressure value of each node is calculated using the Navier-Stokes equation.

In a second aspect, the present disclosure provides a device for obtaining a microcirculation indicator based on an image and a pressure sensor, which is used in the method for calculating a microcirculation indicator based on an image and a pressure sensor, the device comprises: a pressure sensor, a coronary angiography extraction unit, a three-dimensional modeling unit and a parametric measurement unit, the coronary angiography extraction unit being connected to the three-dimensional modeling unit, and the parametric measurement unit being connected to the pressure sensor and the three-dimensional modeling unit;

the pressure sensor being used to measure the coronary artery inlet pressure $P_a$;

the coronary angiography extraction unit being used to select the angiographic image of the first body position and the angiographic image of the second body position of a blood vessel to be measured;

the three-dimensional modeling unit being used to receive the angiographic image of the first body position and the angiographic image of the second body position transmitted by the coronary angiography extraction unit, and obtain a three-dimensional coronary artery vascular model through three-dimensional modeling;

the parametric measurement unit being used to receive the three-dimensional coronary artery vascular model transmitted by the three-dimensional modeling unit, obtain time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position; obtaining the microcirculation indicator according to $T_1$ and $T_2$.

Optionally, in the above device for obtaining a microcirculation indicator based on an image and a pressure sensor, the parametric measurement unit comprises: a CFR measurement module, and the CFR measurement module serves to measure coronary flow reserve CFR, said CFR=$T_1/T_2$; and/or the device for calculating the microcirculation indicator further comprises: a microcirculation resistance index measuring device connected to the parametric measurement unit, the microcirculation resistance index measuring device being used to measure the microcirculation resistance index IMR, IMR=$(P_a-\Delta P_i)\times T_2$; and/or the device for calculating the microcirculation indicator further comprises: a coronary fractional flow reserve measuring device connected to the parametric measurement unit, the coronary fractional flow reserve measuring device being used to measure the coronary fractional flow reserve FFR, FFR=$(P_a-\Delta P_i)/P_a$.

In a third aspect, the present disclosure provides a coronary artery analysis system, comprising: the above device for obtaining a microcirculation indicator based on an image and a pressure sensor.

In a fourth aspect, the present disclosure provides a computer storage medium, when a computer program is executed by a processor to realize the method for calculating a microcirculation indicator based on an image and a pressure sensor.

Advantageous effect brought by embodiments of the present disclosure comprises at least:

the present disclosure provides a method for calculating a microcirculation indicator based on an image and a pressure sensor. The vasodilator is injected only during the angiography. The vasodilator injection may be stopped a few seconds after the start of angiography process, which reduces the injection time of the vasodilator. Next, the coronary angiographic image is subjected to three-dimensional modeling to obtain the time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position in the dilated state; CFR is measured according to $T_1$ and $T_2$ without a pressure wire. The measurement process is simple and the test result is accurate, which overcomes the problem of measuring CFR via the pressure wire.

BRIEF DESCRIPTION OF DRAWINGS

The drawings described here are used to provide a further understanding of the present disclosure and constitute a part of the present disclosure. The exemplary embodiments and descriptions of the present disclosure are used to explain the present disclosure, and do not constitute an improper limitation on the present disclosure. In the drawings.

The reference signs are described below:

pressure sensor 110, baroreceptive chip 1, peristaltic pump head 2, hose 3, luer connector 4, laser emitter 5, display screen 6, one-way valve 7, coronary angiography extraction unit 120, three-dimensional modeling unit 130, image-reading module 131, segmentation module 132, blood vessel length measurement module 133, three-dimensional modeling module 134, image processing module 135, image denoising module 1350, catheter feature point extraction module 1351, coronary extraction module 1352, coronary centerline extraction module 136, blood vessel diameter measurement module 137, parametric measurement unit 140, CFR measurement module 141, microcirculation resistance index measurement device 200, and coronary fractional flow reserve measurement device 300.

DETAILED DESCRIPTION OF PREFERRED EMBODIMENTS

In order to make objectives, technical solutions and advantages of the present disclosure clearer, the technical solutions of the present disclosure will be described clearly and completely below in conjunction with the specific embodiments of the present disclosure and the corresponding drawings. It is apparently that the described embodiments are only a part of the embodiments of the present disclosure, rather than all the embodiments. Based on the embodiments of the present disclosure, all other embodiments obtained by a person skilled in the art without paying creative work shall fall within the protection scope of the present disclosure.

Hereinafter, a number of embodiments of the present disclosure will be disclosed in the form of drawings. For clear description, many practical details will be described in the following description. However, it should be understood that these practical details should not be used to limit the present disclosure. In other words, in some embodiments of the present disclosure, these practical details are unnecessary.

Figure 1:
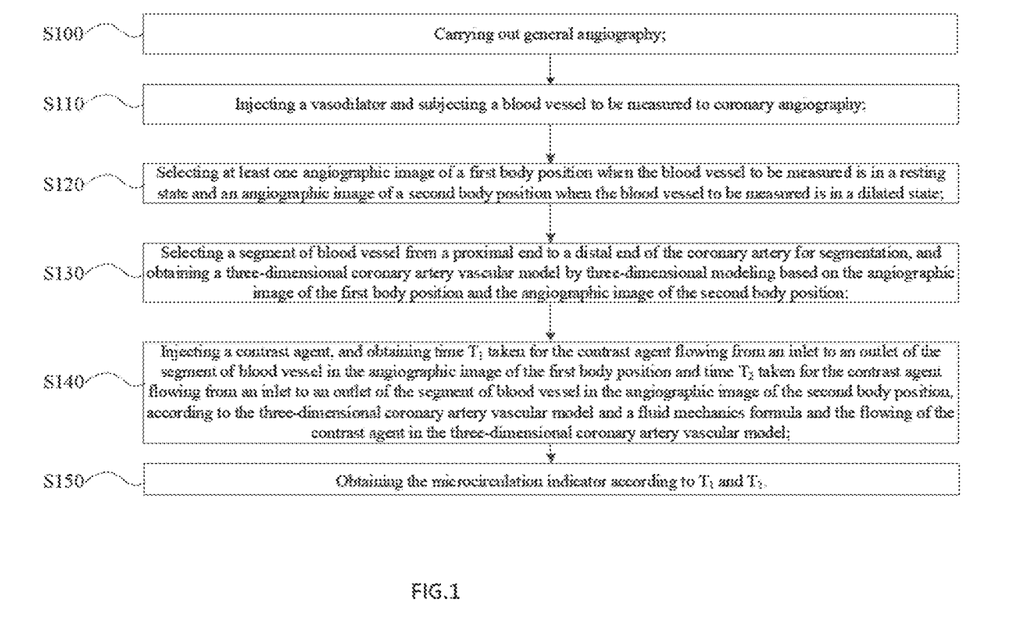
FIG. 1 is a flowchart of an embodiment of a method for calculating a microcirculation indicator based on an image and a pressure sensor of the present disclosure.

As shown in FIG. 1, the present disclosure provides a method for calculating a microcirculation indicator based on an image and a pressure sensor, comprising:

S100, carrying out general angiography;

S110, injecting a vasodilator and subjecting a blood vessel to be measured to coronary angiography;

S120, selecting at least one angiographic image of a first body position when the blood vessel to be measured is in a resting state and an angiographic image of a second body position when the blood vessel to be measured is in a dilated state;

S130, selecting a segment of blood vessel from a proximal end to a distal end of the coronary artery for segmentation, and obtaining a three-dimensional coronary artery vascular model by three-dimensional modeling based on the angiographic image of the first body position and the angiographic image of the second body position;

S140, injecting a contrast agent, and obtaining time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position, respectively, according to the three-dimensional coronary artery vascular model and a fluid mechanics formula and the flowing of the contrast agent in the three-dimensional coronary artery vascular model;

S150: obtaining the microcirculation indicator according to $T_1$ and $T_2$.

The present disclosure provides a method for obtaining coronary artery flow reserve based on angiographic images. The vasodilator is injected only during the angiography. The vasodilator injection may be stopped a few seconds after the start of angiography process, which reduces the injection time of the vasodilator. Next, the coronary angiographic image is subjected to three-dimensional modeling to obtain the time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position in the dilated state; CFR is measured according to $T_1$ and $T_2$ without a pressure wire. The measurement process is simple and the test result is accurate, which overcomes the problem of measuring CFR via the pressure wire.

It should be noted that the injection of the vasodilators comprises: intravenous or intracoronary injection of the vasodilator. The infusion method comprises: the mixture of vasodilator and the contrast agent may be injected into the vein or coronary artery, or injected in several times and at intervals, which fall within the protection scope of the present disclosure; as long as a drugs can perform the function of dilatation, such drugs, including adenosine, ATP and the like, fall within the protection scope of the present disclosure.

In an embodiment of the present disclosure, the microcirculation indicator comprises coronary flow reserve CFR, $CFR=T_1/T_2$. In the present disclosure, the CFR value is obtained through the formula $CFR=T_1/T_2$ based on the angiographic image of the second body position in the dilated state.

In an embodiment of the present disclosure, the times $T_1$ and $T_2$ in S140 are calculated according to a ratio of the number of frames of the partial area image into which the heartbeat cycle area is divided to the number of frames transmitted per second; namely:

T=N/fps, N represents the number of frames of the partial area image into which the heartbeat cycle area is divided, fps represents the number of frames played per second, generally speaking, refers to the number of animation or video frames, T represents the time T taken for the contrast agent flowing from an inlet to an outlet of the segment of blood vessel in the angiographic image of a certain body position, and thus $T_1$ and $T_2$ can be calculated according to the above formula. In an embodiment of the present disclosure, fps=10-30; preferably, fps=15.

Since $T_1$ and $T_2$ are measured based on the three-dimensional coronary artery model obtained from the angiographic image, the CFR is also measured through the three-dimensional coronary artery model without relying on a pressure guide wire sensor, which overcomes the problem of ease of movement for the pressure guide wire sensor under the impact of the saline and the inaccurate measurement, and there is no need to inject saline when the measurement is based on the angiographic image, thereby avoiding the influences of the saline injection speed, injection volume, and temperature of the saline on the CFR measurement results and improving the accuracy of the measurement.

In an embodiment of the present disclosure, an angle between the first body position and the second body position is greater than 30°.

Figure 2:
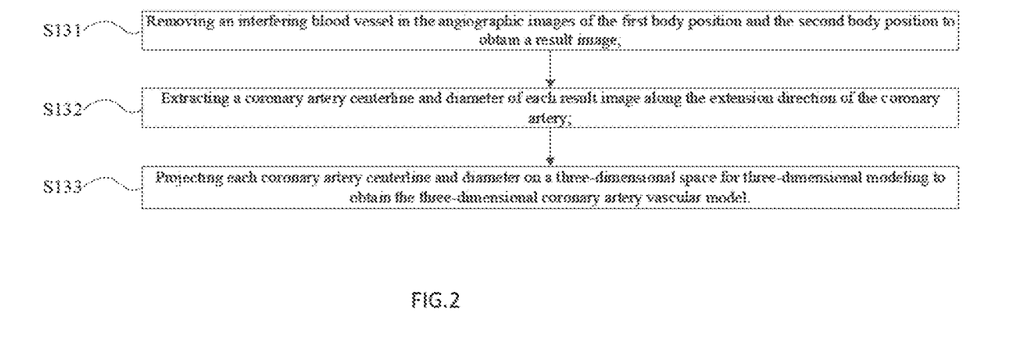
FIG. 2 is a flowchart of step S130 of the present disclosure.

As shown in FIG. 2, in an embodiment of the present disclosure, S130 comprises:

S131: removing an interfering blood vessel in the angiographic images of the first body position and the second body position to obtain a result image, specifically:

removing the interfering blood vessel in the angiographic images of the first body position and the second body position;

denoising coronary angiographic images, including static noise and dynamic noise;

defining the segmented image of the first frame where the catheter appears as a reference image, and defining the segmented image of the k-th frame where a complete coronary artery appears as the target image, and k is a positive integer greater than 1.

The target image is subtracted from the reference image to extract the feature point O of the catheter. The specific method is: subtracting the target image from the reference image; denoising, including static noise and dynamic noise; subjecting image enhancement to the denoised image; subjecting binarization processing to the enhanced catheter image to obtain a binarized image with a set of catheter feature points O;

The reference image is subtracted from the target image to extract the regional image in the position at which the coronary artery is located. The specific method is: subtracting the reference image from the target image; denoising, including static noise and dynamic noise; subjecting image enhancement to the denoised image; according to the positional relationship between each region in the enhanced target image and the feature points of the catheter, determining and extracting the region of the coronary artery, that is, the regional image in the position at which the coronary artery is located.

The regional image uses the feature points of the catheter as seed points for dynamic growth to obtain the result image. The specific method is: subjecting the regional image in the position at which the coronary artery is located to binarization processing to obtain a binary coronary arterial image; subjecting the binary coronary artery image to morphological operations, and using the characteristic points of the catheter as seed points, and carrying out dynamic region growth of the binary coronary artery image according to the position at which the seed point is located to obtain the result image;

S132: extracting the coronary artery centerline and diameter of each result image along the extension direction of the coronary artery;

S133: projecting each coronary artery centerline and diameter on a three-dimensional space for three-dimensional modeling to obtain the three-dimensional coronary artery vascular model. The specific method is:

obtaining the body position shooting angle of each coronary angiographic image;

projecting each coronary artery centerline in combination with the body position shooting angle on a three-dimensional space, and performing projection to generate a three-dimensional coronary artery vascular model.

Figure 3:
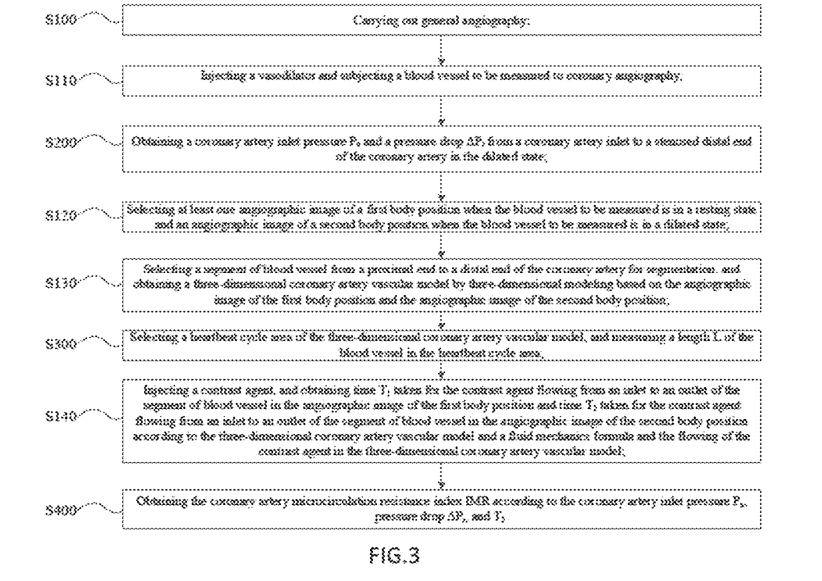
FIG. 3 is a flowchart of another embodiment of a method for calculating a microcirculation indicator based on an image and a pressure sensor according to the present disclosure.

As shown in FIG. 3, in an embodiment of the present disclosure, the microcirculation indicator comprises: coronary artery microcirculation resistance index IMR, and the specific measurement method is:

S100, carrying out general angiography;

S110, injecting a vasodilator and subjecting a blood vessel to be measured to coronary angiography;

S200: obtaining a coronary artery inlet pressure $P_a$ by a pressure sensor and obtaining a pressure drop $\Delta P_i$ from a coronary artery inlet to a stenosed distal end of the coronary artery in the dilated state;

S120, selecting at least one angiographic image of a first body position when the blood vessel to be measured is in a resting state and an angiographic image of a second body position when the blood vessel to be measured is in a dilated state;

S130, selecting a segment of blood vessel from a proximal end to a distal end of the coronary artery for segmentation, and obtaining a three-dimensional coronary artery vascular model by three-dimensional modeling based on the angiographic image of the first body position and the angiographic image of the second body position;

S300: selecting a heartbeat cycle area of the three-dimensional coronary artery vascular model, and measuring the length L of the blood vessel in the heartbeat cycle area;

S140, injecting a contrast agent, and obtaining time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position according to the three-dimensional coronary artery vascular model and a fluid mechanics formula and the flowing of the contrast agent in the three-dimensional coronary artery vascular model;

S400: obtaining the coronary artery microcirculation resistance index IMR according to the coronary artery inlet pressure $P_a$, pressure drop $\Delta P_i$ and $T_2$.

The present disclosure is based on the acquired angiographic image of the second body position in a dilated state, according to IMR=$(P_a-\Delta P_i) \times T_2$; IMR>25 is considered to have a microcirculation disease, which is consistent with the evaluation criteria when the pressure guide wire is used to obtain IMR. However, no pressure guide wire is required in the present disclosure, and the measurement process is simple, which overcomes the problem of measuring IMR via the pressure wire.

In an embodiment of the present disclosure, in S400, measuring the pressure drop $\Delta P_i$ from the coronary artery inlet to the stenosed distal end of the coronary artery comprises:

Subjecting the three-dimensional coronary artery vascular model to a grid division, with the coronary artery centerline as the longitudinal axis, dividing the grid into m points along the coronary artery centerline, and dividing the cross section corresponding to each point of the coronary artery centerline into n nodes, $\Delta P_i$ representing the average value of the pressures of all nodes on the cross section of the i-th point on the coronary center line;

the pressure drop $\Delta P_i$ is calculated using the following formula:

$$\Delta P_i = \frac{\sum_1^n (P_1 + P_2 + \ldots + P_n)}{n};$$

$P_1$ represents the pressure value of the first node on the cross section of the i-th point in the grids of the three-dimensional vascular model, $P_2$ represents the pressure value of the second node on the cross section of the i-th point in the grids of the three-dimensional vascular model, $P_n$ represents the pressure value of the n-th node on the cross section of the i-th point, and both m and n are positive integers;

the pressure value of each node is calculated using the Navier-Stokes equation.

Figure 4:
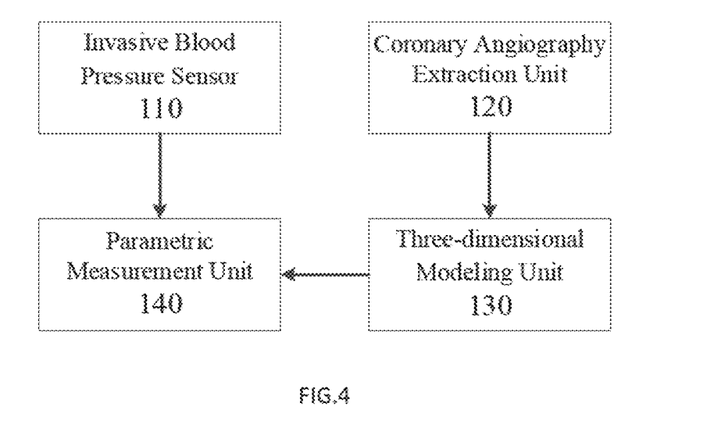
FIG. 4 is a structural block diagram of an embodiment of the device for obtaining a microcirculation indicator based on an image and a pressure sensor of the present disclosure.

As shown in FIG. 4, the present disclosure provides a device for obtaining a microcirculation indicator based on an image and a pressure sensor used in the above-mentioned method for calculating a microcirculation indicator based on an image and a pressure sensor, comprising: a pressure sensor 110, a coronary angiography extraction unit 120, a three-dimensional modeling unit 130 and a parametric measurement unit 140, the coronary angiography extraction unit 120 is connected to the three-dimensional modeling unit 130, and the parametric measurement unit 140 is connected to the pressure sensor 110 and the three-dimensional modeling unit 130; the pressure sensor 110 serves to measure coronary artery inlet pressure $P_a$; the coronary angiography extraction unit 120 serves to select the angiographic image of the first body position and the angiographic image of the second body position of the blood vessel to be measured; the three-dimensional modeling unit 130 serves to receive the angiographic image of the first body position and the angiographic image of the second body position transmitted by the coronary angiography extraction unit 120 and three-dimensionally model to obtain a three-dimensional coronary artery vascular model; the parametric measurement unit 140 serves to receive the three-dimensional coronary artery vascular model transmitted by the three-dimensional modeling unit 130 to obtain the time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position; the coronary flow reserve CFR is obtained according to $T_1$ and $T_2$, CFR=$T_1/T_2$.

The parametric measurement unit 140 comprises: a $T_1$ measurement module, a $T_2$ measurement module, and a CFR measurement module, all of which are connected to the three-dimensional modeling unit 130, and both the $T_1$ measurement module and $T_2$ measurement module are connected to the CFR measurement module.

Figure 5:
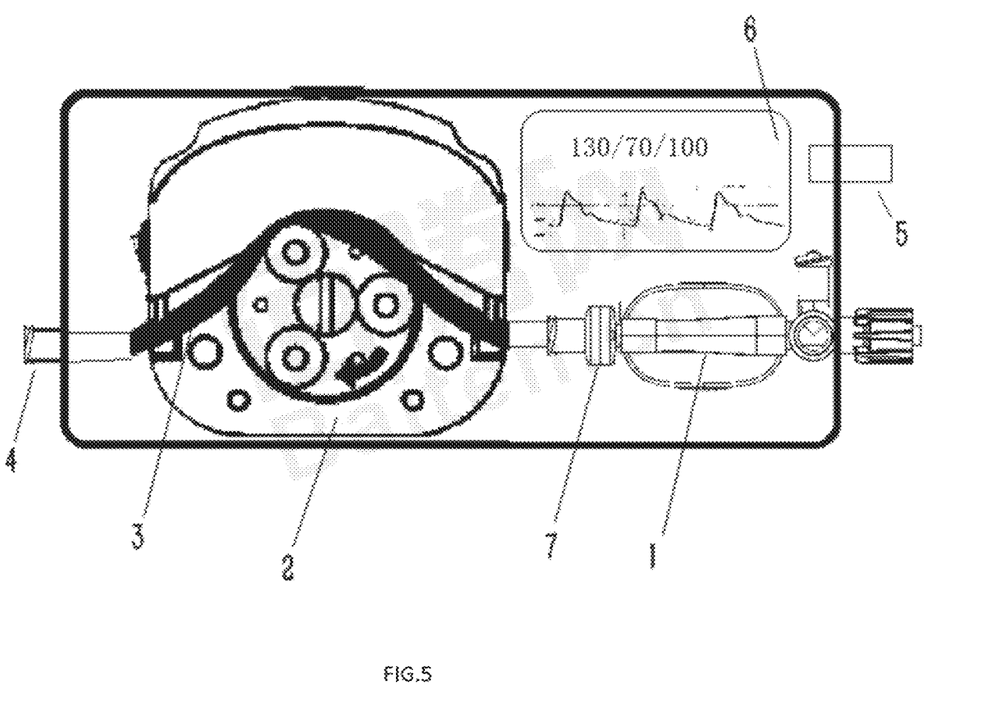
FIG. 5 is a schematic diagram of a structure of a pressure sensor of the disclosure.

As shown in FIG. 5, in an embodiment of the present disclosure, the pressure sensor 110 comprises a baroreceptive chip 1, and also comprises a peristaltic pump head 2. The peristaltic pump head 2 comprises a rotating wheel provided with a connection structure connected to a rotating shaft of an external motor. The peristaltic pump head 2 is equipped with a built-in hose 3 with one end connected to the baroreceptive chip 1 and the other end connected to a saline bag via an infusion tube. One end of the pressure sensor is connected to the saline bag, and the other end is connected to a patient's aorta through an external device. The purpose of the pressure sensor is to connect to the patient's aorta. The middle of the pressure sensor is filled with the saline so that it can form a pathway with the aorta. The baroreceptive chip 1 inside the pressure sensor can convert the dynamic pressure of the aorta into an analog signal, and the collected analog signal can be converted into a digital model through a circuit inside the pressure sensor to obtain the coronary artery inlet pressure $P_a$ of the aortic pressure. The coronary artery inlet pressure $P_a$ uses the average value of the sum of the systolic blood pressure and the diastolic blood pressure; the systolic pressure, diastolic blood pressure and coronary artery inlet pressure $P_a$ are displayed on the display screen 6.

As shown in FIG. 5, in an embodiment of the present disclosure, the end of the hose 3 connecting to the infusion tube is provided with a luer connector 4 and through which the hose 3 is connected to the infusion tube; a one-way valve 7 is connected between the hose 3 and a baroreceptive chip 1. The flowing direction of the one-way valve 7 is allowable from the saline bag to the baroreceptive chip 1; the pressure sensor also comprises a laser emitter 5, which is at the same level as the baroreceptive chip 1. The laser emitter 5 can emit a horizontal beam to irradiate the heart of the patient and ensure that the height of the laser emitter 5 is at the same level as the heart. The beam plays a role in assisting the alignment, making the alignment easier. The baroreceptive chip 1 is designed to be at the same level as the laser emitter 5, so as to ensure that the baroreceptive chip 1 is at the same level as the heart and thus the aortic pressure can be accurately measured.

Figure 6:
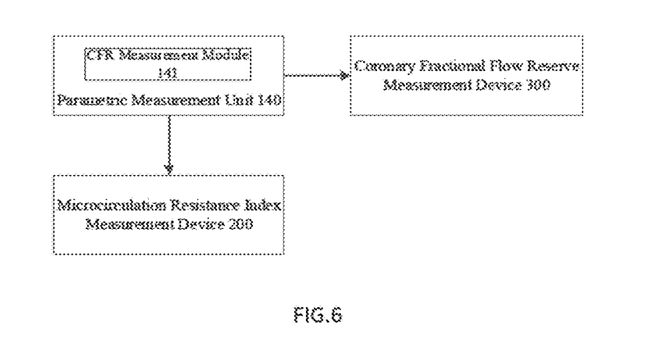
FIG. 6 is a structural block diagram of another embodiment of the device for obtaining a microcirculation indicator based on an image and a pressure sensor of the present disclosure.

As shown in FIG. 6, in an embodiment of the present disclosure, the parametric measurement unit 140 comprises: a CFR measurement module 141, which serves to measure the coronary flow reserve CFR, CFR=$T_1/T_2$; and/or The device for calculating the microcirculation indicator also comprises: a microcirculation resistance index measuring device 200 connected to the parametric measuring unit 140, which serves to measure the microcirculation resistance index IMR, IMR=$(P_a-\Delta P_i) \times T_2$; and/or The device for calculating the microcirculation indicator also comprises: a coronary fractional flow reserve measurement device 300 connected to the parametric measuring unit 140, which serves to measure the coronary fractional flow reserve FFR, FFR=$(P_a-\Delta P_i)/P_a$.

Figure 7:
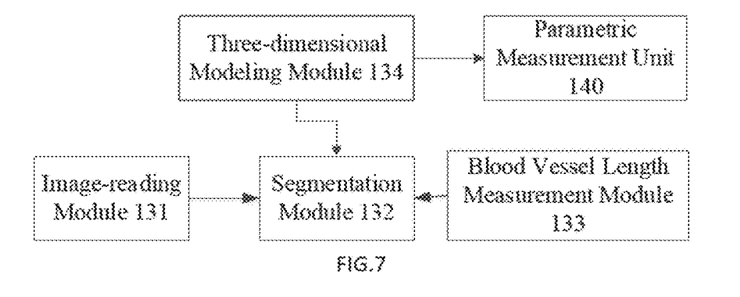
FIG. 7 is a structural block diagram of an embodiment of a three-dimensional modeling unit of the present disclosure.

As shown in FIG. 7, in an embodiment of the present disclosure, the three-dimensional modeling unit 130 comprises an image-reading module 131, a segmentation module 132, a blood vessel length measurement module 133, and a three-dimensional modeling module 134. The segmentation module 132 is connected to the image-reading module 131, the blood vessel length measurement module 133 and the three-dimensional modeling module 134; the image-reading module 131 serves to read the angiographic image; the segmentation module 132 serves to select a heartbeat cycle area of the coronary angiographic image; the blood vessel length measurement module 133 serves to measure the length L of the blood vessel in the heartbeat cycle area, and transmit the length L of the blood vessel to the segmentation module 132; the three-dimensional modeling module 134 serves to subject the coronary angiographic image selected by the segmentation module 132 to three-dimensional modeling so as to obtain the three-dimensional coronary vascular model.

Figure 8:
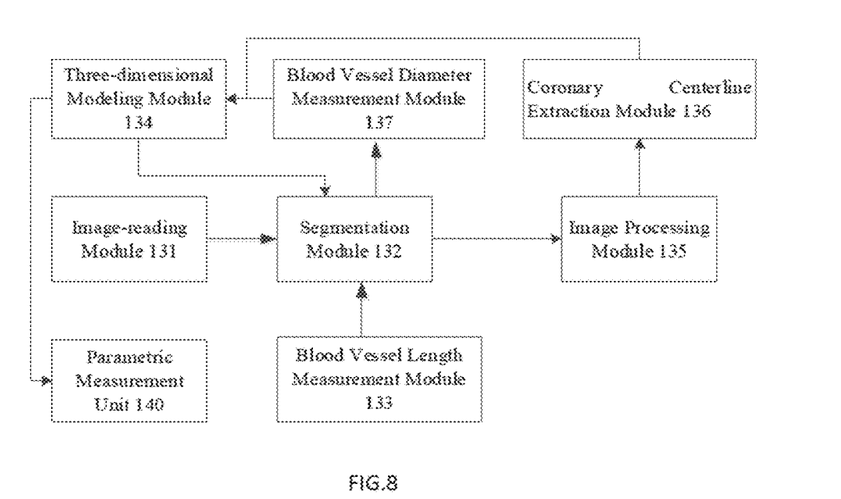
FIG. 8 is a structural block diagram of another embodiment of the three-dimensional modeling unit of the present disclosure.
Figure 17:
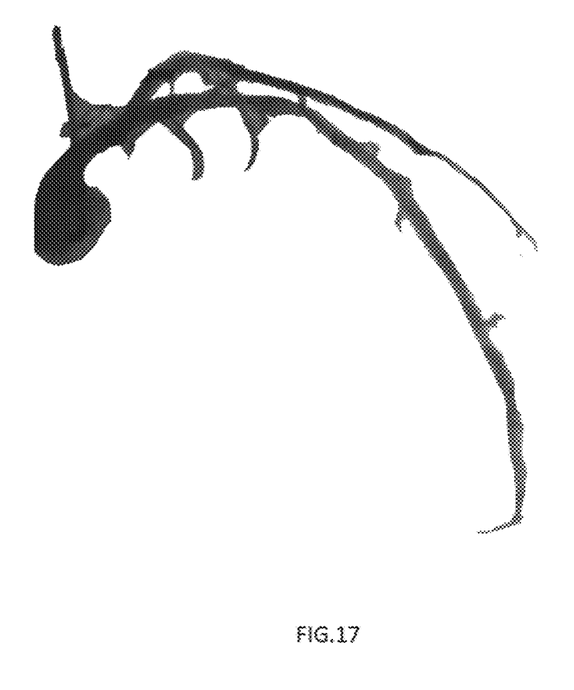
FIG. 17 is a result image.

As shown in FIG. 8, in an embodiment of the present disclosure, the three-dimensional modeling unit 130 further comprises: an image processing module 135, a coronary centerline extraction module 136, and a blood vessel diameter measurement module 137. The image processing module 135 is connected to the coronary centerline extraction module 136, and the three-dimensional modeling module 134 is connected to the coronary centerline extraction module 136 and the blood vessel diameter measurement module 137. The image processing module 135 serves to receive the coronary angiographic images of at least two body positions transmitted by the segmentation module 132, and remove a interfering blood vessel from the coronary angiographic images to obtain the result image as shown in FIG. 17; the coronary centerline extraction module 136 serves to extract the coronary centerline of each result image as shown in FIG. 17 along the extending direction of the coronary artery; the blood vessel diameter measurement module 137 serves to measure the blood vessel diameter D; the three-dimensional modeling module 134 serves to project centerline and diameter of each coronary artery on the three-dimensional space for three-dimensional modeling, thereby obtaining the three-dimensional coronary vascular model. The present disclosure realizes the synthesis of a three-dimensional coronary vascular model based on coronary angiographic images, which fills up the gap in the industry, and has a positive effect on the medical technology field.

In an embodiment of the present disclosure, an image denoising module 1350 is provided inside the image processing module 135 to denoise the coronary angiographic image, including static noise and dynamic noise. The denoising module 1350 removes interfering factors in the coronary angiographic image and improves the quality of image processing.

Figure 9:
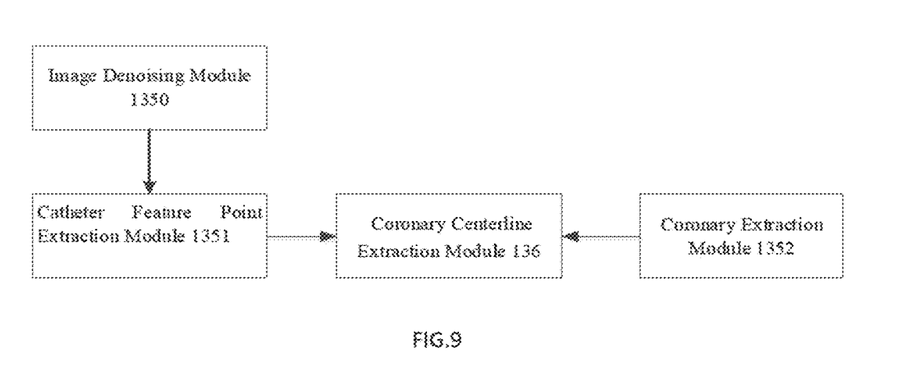
FIG. 9 is a structural block diagram of an image processing module of the present disclosure.
Figure 10:
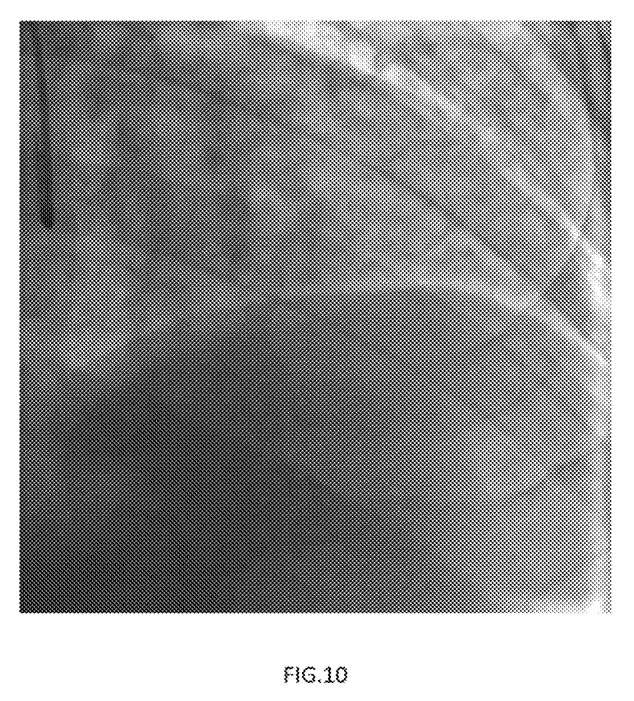
FIG. 10 is a reference image.
Figure 11:
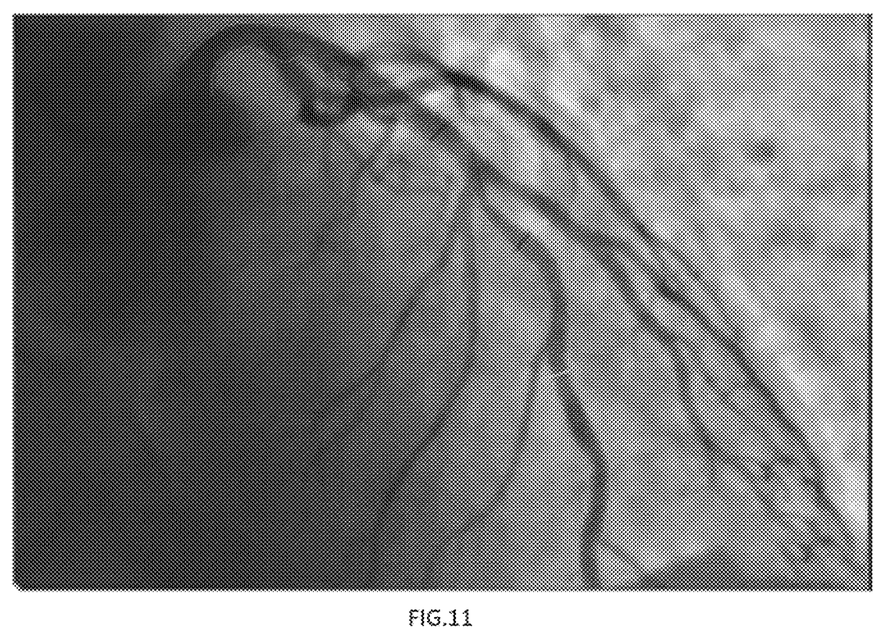
FIG. 11 is a target image to be segmented.
Figure 12:
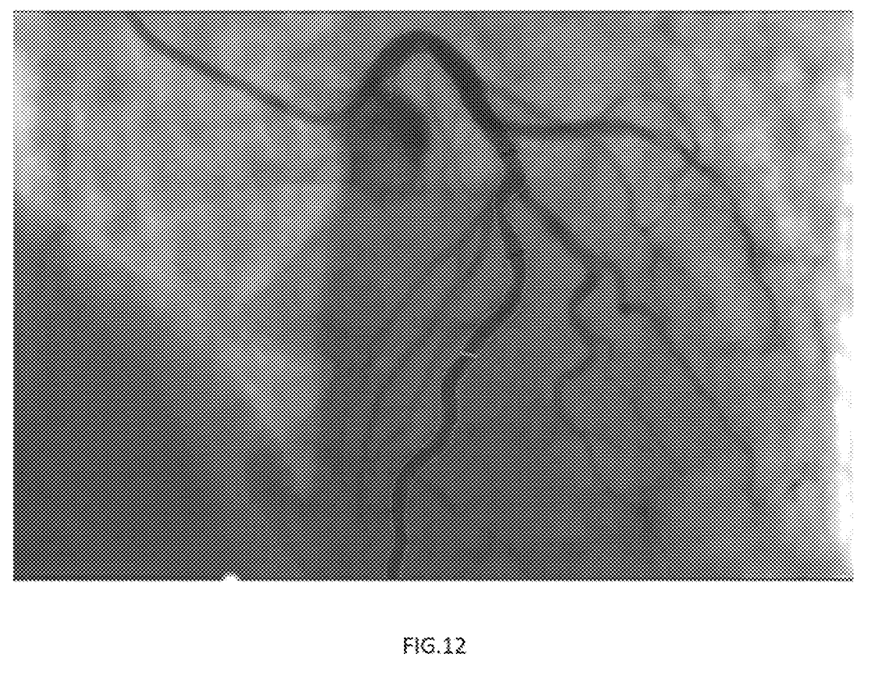
FIG. 12 is another target image to be segmented.
Figure 13:
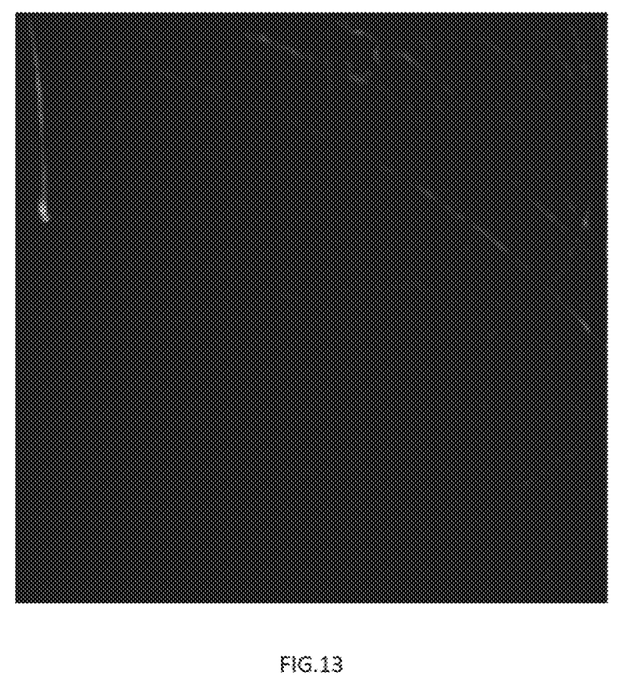
FIG. 13 is an enhanced catheter image.
Figure 14:
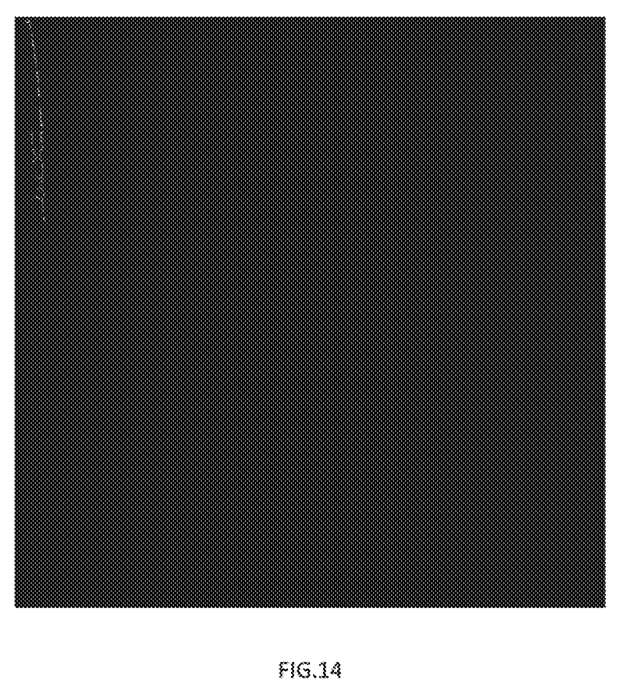
FIG. 14 is a binarized image of catheter feature points.
Figure 15:
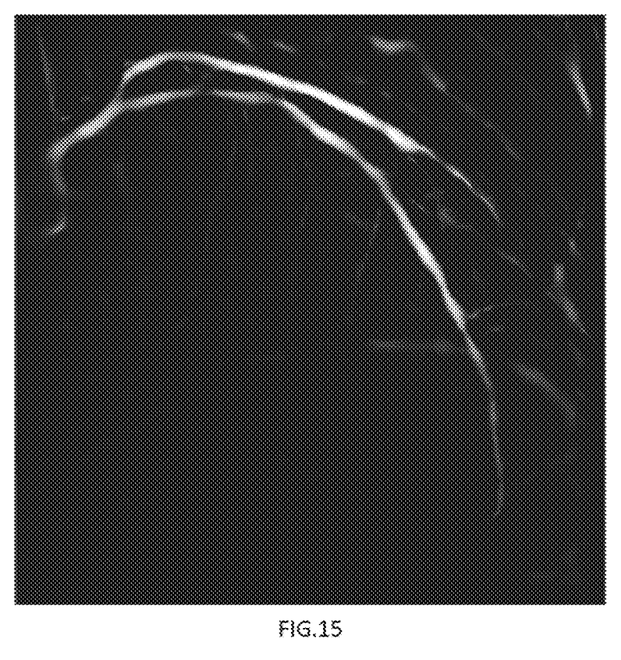
FIG. 15 is an enhanced target image.
Figure 16:
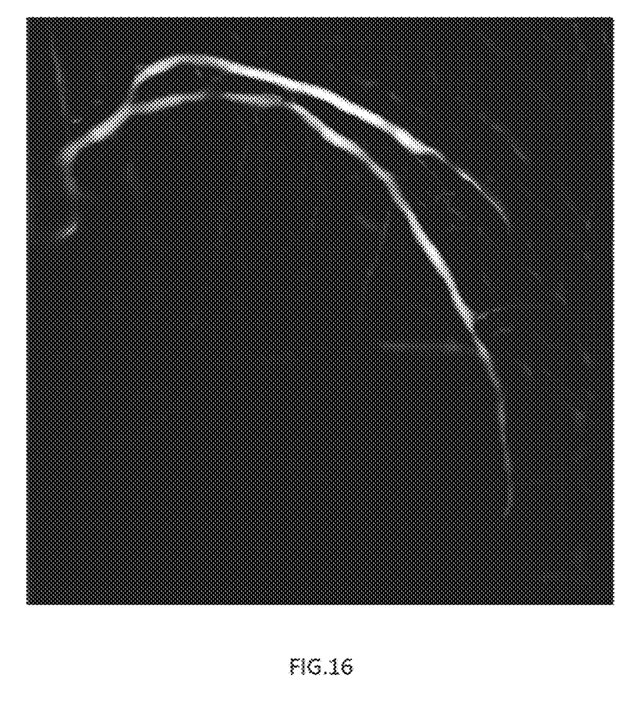
FIG. 16 is an image of the area where the coronary artery is located.

As shown in FIG. 9, in an embodiment of the present disclosure, the image processing module 135 is internally provided with a catheter feature point extraction module 1351 and a coronary extraction module 1352, both of which are connected to the coronary centerline extraction module 136, and the catheter feature point extraction module 1351 is connected to the coronary extraction module 1352 and the image denoising module 1350; the catheter feature point extraction module 1351 serves to define a first frame segmented image where the catheter appears as a reference image shown in FIG. 10, and to define the k-th frame segmented image where the complete coronary artery appears as a target image shown in FIG. 11 and FIG. 12, and k is a positive integer greater than 1. The target images shown in FIGS. 11 and 12 are enhanced to obtain the enhanced images shown in FIGS. 13 and 15; the target images shown in FIG. 11 and FIG. 12 are subtracted from the reference image shown in FIG. 10 to extract the feature point O of the catheter shown in FIG. 14; the coronary extraction module 1352 serves to subtract the reference image shown in FIG. 10 from the target images shown in FIG. 11 and FIG. 12, and the area of the coronary artery is determined and extracted according to the positional relationship between each region and the catheter feature point in the enhanced target image shown in FIG. 15, namely the area image where the coronary artery are located as shown in FIG. 16; the area image shown in FIG. 16 uses the catheter feature point as shown in FIG. 14 as a seed point for dynamic growth to obtain the resulting image as shown in FIG. 17.

The image processing module 135 is also provided with a binarization processing module for binarizing the image to obtain a three-dimensional coronary vascular model.

Figure 18:
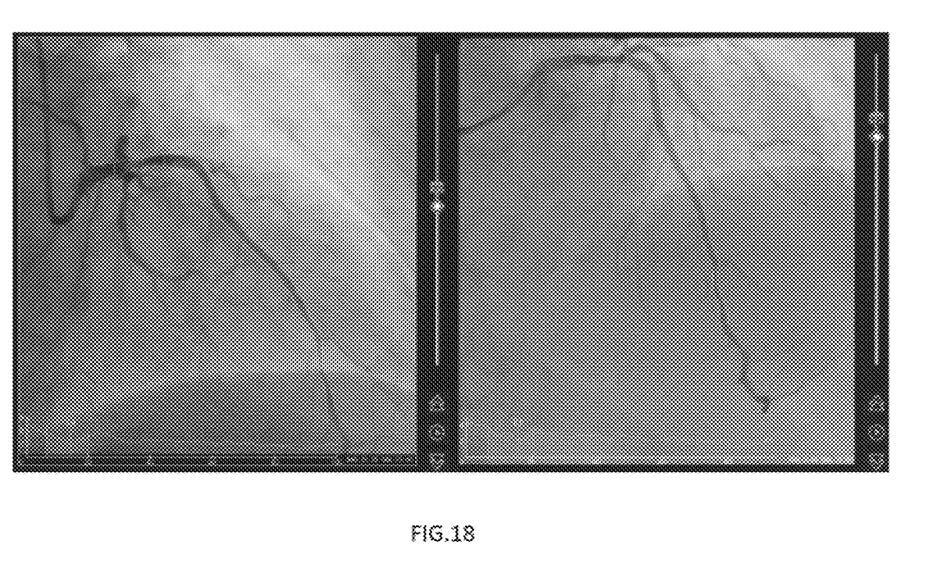
FIG. 18 shows angiographic images of two body positions.
Figure 19:
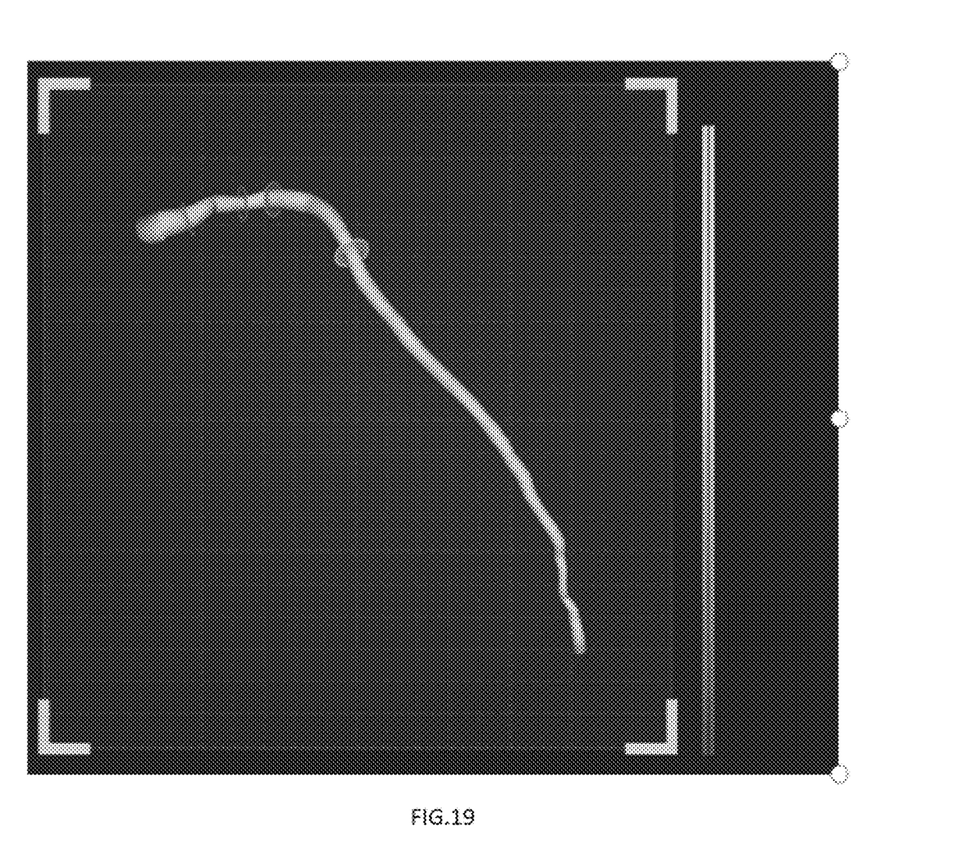
FIG. 19 is a diagram of a three-dimensional coronary artery vascular model generated by combining FIG. 18 with the angle of the body positions and the coronary centerline.

The disclosure will be specifically described below in conjunction with specific examples:

Example 1:

As shown in FIG. 18, it is a coronary angiographic image of two body positions taken for a patient; the left image is the angiographic image with the right anterior oblique RAO: 25° and the head position CRA: 23°; the right image is the angiographic image in the dilated state with body position angle being right anterior oblique RAO: 3° and head position CRA: 30°;

The blood vessel length L value of the three-dimensional coronary vascular model=120 mm; the generated three-dimensional coronary vascular model is shown in FIG. 19;

vascular diameter D value=2~4 mm, $P_a$=104 mmHg; T2=$N_2$/$fps_2$=9/15=0.6 s; $T_1$=$N_1$/$fps_1$=20/15=1.3 s;

$$CFR=T_1/T_2=1.3/0.6=2.17;$$

$\Delta P$=2; therefore, IMR=$(104-2) \times 0.6$=61.2;

Comparative Example 1:

the patient is the same as in Example 1, and both Comparative Example 1 and Example 1 use the same coronary angiographic image taken for the same patient;

A pressure guide wire sensor was placed on a distal end of the coronary artery of the patient (>5 cm distanced from the opening of the guiding catheter), and 3 ml of saline is injected into the blood vessel through the catheter. If the blood temperature is detected to return to the normal value, 3 ml of normal saline will be injected into the blood vessel again via the catheter, and the above process is repeated for 3 times, and then $T_1$ is recorded and $T_1$ is 1.28 s; the vasodilator is delivered into the blood vessel to make the blood vessel reach and maintain the dilated state (ensure that the pressure guide wire sensor before and after the vasodilator injection is in the same position), 3 ml of saline is injected into the blood vessel through the catheter. If it is detected that the blood temperature returns to the normal value, 3 ml of saline is injected into the blood vessel through the catheter again, the above process is repeated for 3 times, and then $T_2$ is recorded, and $T_2$ is 0.58 s, the pressure at the distal end of the coronary artery is measured as $P_d$=103.5 mmHg;

$$CFR=1.28/0.58=2.21;$$

$$IMR=P_d \times T_2=103.5 \times 0.6=60.03;$$

Compared Example 1 with Comparative Example 1, it can be seen that the IMR measurement results are basically the same. Therefore, the measurement results of Example 1 are accurate, and the examples of the present disclosure does not require a pressure wire, only needs to measure the coronary inlet pressure without passing through the stenotic distal end of the coronary artery, which brings the advantages of reducing the difficulty and risk of surgery; and realizing the measurement of IMR through angiographic images, and making up for the gap in the industry and making the operation easier.

The present disclosure provides a coronary artery analysis system, comprising: the above-mentioned device for obtaining a microcirculation indicator based on an image and a pressure sensor.

The present disclosure provides a computer storage medium. The aforementioned method for calculating a microcirculation indicator based on an image and a pressure sensor is realized when a computer program is executed by a processor.

A person skilled in the art knows that various aspects of the present disclosure can be implemented as a system, a method, or a computer program product. Therefore, each aspect of the present disclosure can be specifically implemented in the following forms, namely: complete hardware implementation, complete software implementation (including firmware, resident software, microcode, etc.), or a combination of hardware and software implementations, here can be collectively referred to as "circuit", "module" or "system". In addition, in some embodiments, various aspects of the present disclosure may also be implemented in the form of a computer program product in one or more computer-readable media, and the computer-readable medium contains computer-readable program code. Implementation of methods and/or systems of embodiments of the present disclosure may involve performing or completing selected tasks manually, automatically, or a combination thereof.

For example, hardware for performing selected tasks according to an embodiment of the present disclosure may be implemented as a chip or a circuit. As software, selected tasks according to an embodiment of the present disclosure can be implemented as a plurality of software instructions executed by a computer using any suitable operating system. In an exemplary embodiment of the present disclosure, a data processor performs one or more tasks according to an exemplary embodiment of a method and/or system as described herein, such as a computing platform for executing multiple instructions. Optionally, the data processor comprises a volatile memory for storing instructions and/or data and/or a non-volatile memory for storing instructions and/or data, for example, a magnetic hard disk and/or movable medium. Optionally, a network connection is also provided. Optionally, a display and/or user input device, such as a keyboard or mouse, are/is also provided.

Any combination of one or more computer readable can be utilized. The computer-readable medium may be a computer-readable signal medium or a computer-readable storage medium. The computer-readable storage medium may be, for example, but not limited to, an electrical, magnetic, optical, electromagnetic, infrared, or semiconductor system, apparatus, or device, or any combination of the above. More specific examples (non-exhaustive list) of computer-readable storage media would include the following:

Electrical connection with one or more wires, portable computer disk, hard disk, random access memory (RAM), read only memory (ROM), erasable programmable read only memory (EPROM or flash memory), optical fiber, portable compact disk read only memory (CD-ROM), optical storage device, magnetic storage device, or any suitable combination of the above. In this document, the computer-readable storage medium can be any tangible medium that contains or stores a program, and the program can be used by or in combination with an instruction execution system, apparatus, or device.

The computer-readable signal medium may include a data signal propagated in baseband or as a part of a carrier wave, and computer-readable program code is carried therein. This propagated data signal can take many forms, including but not limited to electromagnetic signals, optical signals, or any suitable combination of the above. The computer-readable signal medium may also be any computer-readable medium other than the computer-readable storage medium. The computer-readable medium may send, propagate, or transmit the program for use by or in combination with the instruction execution system, apparatus, or device.

The program code contained on the computer-readable medium can be transmitted by any suitable medium, including, but not limited to, wireless, wired, optical cable, RF, etc., or any suitable combination of the above.

For example, any combination of one or more programming languages can be used to write computer program codes for performing operations for various aspects of the present disclosure, including object-oriented programming languages such as Java, Smalltalk, C++, and conventional process programming languages, such as "C" programming language or similar programming language. The program code can be executed entirely on the user's computer, partly on the user's computer, executed as an independent software package, partly on the user's computer and partly executed on a remote computer, or entirely executed on the remote computer or server. In the case of a remote computer, the remote computer can be connected to the user's computer through any kind of network including a local area network (LAN) or a wide area network (WAN), or it can be connected to an external computer (for example, connected through Internet provided by an Internet service provider).

It should be understood that each block of the flowcharts and/or block diagrams and combinations of blocks in the flowcharts and/or block diagrams can be implemented by computer program instructions. These computer program instructions can be provided to the processors of general-purpose computers, special-purpose computers, or other programmable data processing devices to produce a machine, which produces a device that implements the functions/actions specified in one or more blocks in the flowchart and/or block diagram when these computer program instructions are executed by the processors of the computer or other programmable data processing devices.

It is also possible to store these computer program instructions in a computer-readable medium. These instructions make computers, other programmable data processing devices, or other devices work in a specific manner, so that the instructions stored in the computer-readable medium generate an article of manufacture that implements instructions for the functions/actions specified in one or more blocks in the flowcharts and/or block diagrams.

Computer program instructions can also be loaded onto a computer (for example, a coronary artery analysis system) or other programmable data processing equipment to facilitate a series of operation steps to be performed on the computer, other programmable data processing equipment or other equipment to produce a computer-implemented process, which enable instructions executed on a computer, other programmable device, or other equipment to provide a process for implementing the functions/actions specified in the flowchart and/or one or more block diagrams.

The above specific examples of the present disclosure further describe the purpose, technical solutions and beneficial effects of the present disclosure in further detail. It should be understood that the above are only specific embodiments of the present disclosure and are not intended to limit the present disclosure. Within the spirit and principle of the present disclosure, any modification, equivalent replacement, improvement, etc. shall be included in the protection scope of the present disclosure.

What is claimed is:

1. A method for calculating a microcirculation indicator based on an image and a pressure sensor comprising:
   carrying out general angiography;
   injecting a vasodilator and subjecting a blood vessel to be measured to coronary angiography;
   selecting at least one angiographic image of a first body position when the blood vessel to be measured is in a resting state and an angiographic image of a second body position when the blood vessel to be measured is in a dilated state;
   selecting a segment of blood vessel from a proximal end to a distal end of the coronary artery for segmentation, and obtaining a three-dimensional coronary artery vascular model by three-dimensional modeling based on the angiographic image of the first body position and the angiographic image of the second body position;
   injecting a contrast agent, and obtaining time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position, respectively, according to the three-dimensional coronary artery vascular model and a fluid mechanics formula and the flowing of the contrast agent in the three-dimensional coronary artery vascular model; and
   obtaining the microcirculation indicator according to $T_1$ and $T_2$;
   wherein the microcirculation indicator comprises: coronary artery microcirculation resistance index IMR;
   measuring a coronary artery inlet pressure $P_a$ by the pressure sensor to obtain a pressure drop $\Delta P_i$ from a coronary artery inlet to a stenosed distal end of the coronary artery in the dilated state;
   obtaining the coronary artery microcirculation resistance index IMR according to the coronary artery inlet pressure $P_a$, pressure drop $\Delta P_i$, and $T_2$, wherein the IMR=$(P_a-\Delta P_i) \times T_2$; and
   wherein measuring the pressure drop $\Delta P_i$ from the coronary artery inlet to the stenosed distal end of the coronary artery comprises:
   subjecting the three-dimensional coronary artery vascular model to a grid division, with the coronary artery centerline as the longitudinal axis, dividing the grid into m points along the coronary artery centerline, and dividing the cross section corresponding to each point of the coronary artery centerline into n nodes, $\Delta P_i$ representing the average value of the pressures of all nodes on the cross section of the i-th point on the coronary center line; the pressure drop $\Delta P_i$ is calculated using the following formula:

$$\Delta P_i = \frac{\sum_1^n (P_1 + P_2 + \ldots + P_n)}{n};$$

$P_1$ represents the pressure value of the first node on the cross section of the i-th point in the grids of the three-dimensional vascular model, $P_2$ represents the pressure value of the second node on the cross section of the i-th point in the grids of the three-dimensional vascular model, $P_n$ represents the pressure value of the n-th node on the cross section of the i-th point, and both m and n are positive integers;
   the pressure value of each node is calculated using the Navier-Stokes equation.

2. The method for calculating a microcirculation indicator based on the image and the pressure sensor according to claim 1, wherein the microcirculation indicator comprises coronary flow reserve CFR, and the CFR=$T_1/T_2$.

3. The method for calculating a microcirculation indicator based on the image and the pressure sensor according to claim 1, wherein the times T1 and T2 are calculated according to a ratio of the number of frames of the partial area image into which the heartbeat cycle area is divided to the number of frames transmitted per second.

4. The method for calculating a microcirculation indicator based on the image and the pressure sensor according to claim 1, wherein an angle between the first body position and the second body position is greater than 30°.

5. The method for calculating a microcirculation indicator based on the image and the pressure sensor according to claim 1, wherein obtaining the three-dimensional coronary artery vascular model by three-dimensional modeling based on the angiographic image of the first body position and the angiographic image of the second body position comprises:
   removing a interfering blood vessel in the angiographic images of the first body position and the second body position to obtain a result image;
   extracting the coronary artery centerline and diameter of each result image along the extension direction of the coronary artery;
   projecting each coronary artery centerline and diameter on a three-dimensional space for three-dimensional modeling to obtain the three-dimensional coronary artery vascular model.

6. A device for obtaining a microcirculation indicator based on an image and a pressure sensor, which is used in the method for calculating a microcirculation indicator based on the image and the pressure sensor according to claim 1, wherein the device comprises: a pressure sensor, a coronary angiography extraction unit, a three-dimensional modeling unit and a parametric measurement unit, the coronary angiography extraction unit being connected to the three-dimensional modeling unit, and the parametric measurement unit being connected to the pressure sensor and the three-dimensional modeling unit;

the pressure sensor being used to measure the coronary artery inlet pressure $P_a$;

the coronary angiography extraction unit being used to select the angiographic image of the first body position and the angiographic image of the second body position of a blood vessel to be measured;

the three-dimensional modeling unit being used to receive the angiographic image of the first body position and the angiographic image of the second body position transmitted by the coronary angiography extraction unit, and obtain a three-dimensional coronary artery vascular model through three-dimensional modeling;

the parametric measurement unit being used to receive the three-dimensional coronary artery vascular model transmitted by the three-dimensional modeling unit, obtain time $T_1$ taken for the contrast agent flowing from an inlet to an outlet of the segment of blood vessel in the angiographic image of the first body position and time $T_2$ taken for the contrast agent flowing from an inlet to an outlet of the segment of blood vessel in the angiographic image of the second body position; obtaining the microcirculation indicator according to T1 and T2;

wherein the microcirculation indicator comprises coronary artery microcirculation resistance index IMR, and the device for obtaining the microcirculation indicator further comprises: a microcirculation resistance index measuring device connected to the parametric measurement unit, the microcirculation resistance index measuring device being used to measure the microcirculation resistance index IMR, IMR=$(P_a-\Delta P_i) \times T_2$ where $\Delta P_i$ indicates a pressure drop from the coronary artery inlet to the stenosed distal end of the coronary artery;

wherein the pressure drop $\Delta P_i$ is measured by:

subjecting the three-dimensional coronary artery vascular model to a grid division, with the coronary artery centerline as the longitudinal axis, dividing the grid into m points along the coronary artery centerline, and dividing the cross section corresponding to each point of the coronary artery centerline into n nodes, $\Delta P_i$ representing the average value of the pressures of all nodes on the cross section of the i-th point on the coronary center line; the pressure drop $\Delta P_i$ is calculated using the following formula:

$$\Delta P_i = \frac{\sum_{1}^{n}(P_1 + P_2 + \ldots + P_n)}{n};$$

$P_1$ represents the pressure value of the first node on the cross section of the i-th point in the grids of the three-dimensional vascular model, $P_2$ represents the pressure value of the second node on the cross section of the i-th point in the grids of the three-dimensional vascular model, $P_n$ represents the pressure value of the n-th node on the cross section of the i-th point, and both m and n are positive integers; and the pressure value of each node is calculated using the Navier-Stokes equation.

7. The device for obtaining a microcirculation indicator based on the image and the pressure sensor according to claim 6, wherein the parametric measurement unit comprises: a CFR measurement module, and the CFR measurement module serves to measure coronary flow reserve CFR, said CFR=$T_1/T_2$; and/or the device for obtaining the microcirculation indicator further comprises: a coronary fractional flow reserve measuring device connected to the parametric measurement unit, the coronary fractional flow reserve measuring device being used to measure the coronary fractional flow reserve FFR, FFR=$(P_a-\Delta P_i)/P_a$.

8. A coronary artery analysis system comprising: the device for obtaining a microcirculation indicator based on the image and the pressure sensor according to claim 6.

9. A non-transitory computer readable storage medium, characterized in that, when a computer program is executed by a processor to realize the method for calculating a microcirculation indicator based on the image and the pressure sensor according to claim 1.

* * * * *